(12) United States Patent
Demmer et al.

(10) Patent No.: US 6,491,869 B1
(45) Date of Patent: Dec. 10, 2002

(54) METHOD FOR PREPARING ASSAY SUPPORTS HAVING AN ORDERED SET OF REACTION ZONES

(75) Inventors: Wolfgang Demmer, Göttingen (DE); Dietmar Nussbaumer, Göttingen (DE); Khuong To Vinh, Bockenem (DE); Thang Thuong Nguyen, Vienne en Val (FR); Edwige Bonfils, Strasbourg (FR); Daniel Dupret, Haguenau (FR)

(73) Assignee: Sartorius AG, Gottingen (DE)

( * ) Notice: Subject to any disclaimer, the term of this patent is extended or adjusted under 35 U.S.C. 154(b) by 0 days.

(21) Appl. No.: 09/214,244

(22) PCT Filed: Jun. 25, 1997

(86) PCT No.: PCT/FR97/01132

§ 371 (c)(1),
(2), (4) Date: May 10, 1999

(87) PCT Pub. No.: WO97/49834

PCT Pub. Date: Dec. 31, 1997

(30) Foreign Application Priority Data

Jun. 27, 1996 (FR) .............................. 96 08028

(51) Int. Cl.⁷ ................................................ G01N 33/48
(52) U.S. Cl. ........................... 422/58; 422/61; 436/86; 436/169
(58) Field of Search ............................. 422/56, 58, 61; 436/169, 86, 93, 94

(56) References Cited

U.S. PATENT DOCUMENTS

| | | | | |
|---|---|---|---|---|
| 3,915,639 A | * | 10/1975 | Friedenberg | 422/61 |
| 4,472,498 A | * | 9/1984 | Masuda et al. | 422/56 |
| 4,587,102 A | * | 5/1986 | Nagatomo et al. | 422/56 |
| 4,870,005 A | * | 9/1989 | Akiyoshi et al. | 422/56 |
| 5,270,166 A | * | 12/1993 | Parsons et al. | 436/901 |
| 5,310,650 A | * | 5/1994 | McMahon et al. | 422/947 |
| 5,556,789 A | * | 9/1996 | Goerlach-Graw et al. | 436/169 |

FOREIGN PATENT DOCUMENTS

| | | |
|---|---|---|
| EP | 0 063 810 | 11/1982 |
| WO | WO 89 10977 | 11/1989 |
| WO | WO 94 12670 | 6/1994 |
| WO | WO 95 30774 | 11/1995 |

* cited by examiner

*Primary Examiner*—Lyle A. Alexander
(74) *Attorney, Agent, or Firm*—Hoffman & Baron, LLP; Irving M. Feit

(57) ABSTRACT

The abstract discloses a method for preparing supports for the assay of chemical or biological substances, consisting in preparing N different supports, each being homogeneous for a type of reaction, then in mutually combining, according to a predetermined arrangement, all or part of the said homogenous N supports to constitute assay supports having each an ordered set of reaction zones of N different types or less. The invention also concerns the assay supports prepared by this method and their use in processes of immunological hybridisation assays.

16 Claims, 4 Drawing Sheets

FIG. 1

| 1 | 1 | 1 | 1 | 1 | 1 | 1 | 1 | 1 |
|---|---|---|---|---|---|---|---|---|
| 1 | 1 | 1 | 1 | 1 | 1 | 1 | 1 | 1 |
| 1 | 1 | 1 | 1 | 1 | 1 | 1 | 1 | 1 |
| 1 | 1 | 1 | 1 | 1 | 1 | 1 | 1 | 1 |
| 1 | 1 | 1 | 1 | 1 | 1 | 1 | 1 | 1 |
| 1 | 1 | 1 | 1 | 1 | 1 | 1 | 1 | 1 |
| 1 | 1 | 1 | 1 | 1 | 1 | 1 | 1 | 1 |
| 1 | 1 | 1 | 1 | 1 | 1 | 1 | 1 | 1 |
| 1 | 1 | 1 | 1 | 1 | 1 | 1 | 1 | 1 |
| 1 | 1 | 1 | 1 | 1 | 1 | 1 | 1 | 1 |
| 1 | 1 | 1 | 1 | 1 | 1 | 1 | 1 | 1 |
| 1 | 1 | 1 | 1 | 1 | 1 | 1 | 1 | 1 |
| 1 | 1 | 1 | 1 | 1 | 1 | 1 | 1 | 1 |
| 1 | 1 | 1 | 1 | 1 | 1 | 1 | 1 | 1 |
| 1 | 1 | 1 | 1 | 1 | 1 | 1 | 1 | 1 |

FIG. 2

| 2 | 2 | 2 | 2 | 2 | 2 | 2 | 2 | 2 |
|---|---|---|---|---|---|---|---|---|
| 2 | 2 | 2 | 2 | 2 | 2 | 2 | 2 | 2 |
| 2 | 2 | 2 | 2 | 2 | 2 | 2 | 2 | 2 |
| 2 | 2 | 2 | 2 | 2 | 2 | 2 | 2 | 2 |
| 2 | 2 | 2 | 2 | 2 | 2 | 2 | 2 | 2 |
| 2 | 2 | 2 | 2 | 2 | 2 | 2 | 2 | 2 |
| 2 | 2 | 2 | 2 | 2 | 2 | 2 | 2 | 2 |
| 2 | 2 | 2 | 2 | 2 | 2 | 2 | 2 | 2 |
| 2 | 2 | 2 | 2 | 2 | 2 | 2 | 2 | 2 |
| 2 | 2 | 2 | 2 | 2 | 2 | 2 | 2 | 2 |
| 2 | 2 | 2 | 2 | 2 | 2 | 2 | 2 | 2 |
| 2 | 2 | 2 | 2 | 2 | 2 | 2 | 2 | 2 |
| 2 | 2 | 2 | 2 | 2 | 2 | 2 | 2 | 2 |
| 2 | 2 | 2 | 2 | 2 | 2 | 2 | 2 | 2 |
| 2 | 2 | 2 | 2 | 2 | 2 | 2 | 2 | 2 |

FIG. 3

| N | N | N | N | N | N | N | N | N |
|---|---|---|---|---|---|---|---|---|
| N | N | N | N | N | N | N | N | N |
| N | N | N | N | N | N | N | N | N |
| N | N | N | N | N | N | N | N | N |
| N | N | N | N | N | N | N | N | N |
| N | N | N | N | N | N | N | N | N |
| N | N | N | N | N | N | N | N | N |
| N | N | N | N | N | N | N | N | N |
| N | N | N | N | N | N | N | N | N |
| N | N | N | N | N | N | N | N | N |
| N | N | N | N | N | N | N | N | N |
| N | N | N | N | N | N | N | N | N |
| N | N | N | N | N | N | N | N | N |
| N | N | N | N | N | N | N | N | N |
| N | N | N | N | N | N | N | N | N |

FIG. 4

| 1 | 2 | 3 | 4 | 5 | 6 | 7 | 8 |
|---|---|---|---|---|---|---|---|
| 1 | 2 | 3 | 4 | 5 | 6 | 7 | 8 |
| 1 | 2 | 3 | 4 | 5 | 6 | 7 | 8 |
| 1 | 2 | 3 | 4 | 5 | 6 | 7 | 8 |
| 1 | 2 | 3 | 4 | 5 | 6 | 7 | 8 |
| 1 | 2 | 3 | 4 | 5 | 6 | 7 | 8 |
| 1 | 2 | 3 | 4 | 5 | 6 | 7 | 8 |
| 1 | 2 | 3 | 4 | 5 | 6 | 7 | 8 |
| 1 | 2 | 3 | 4 | 5 | 6 | 7 | 8 |
| 1 | 2 | 3 | 4 | 5 | 6 | 7 | 8 |
| 1 | 2 | 3 | 4 | 5 | 6 | 7 | 8 |
| 1 | 2 | 3 | 4 | 5 | 6 | 7 | 8 |
| 1 | 2 | 3 | 4 | 5 | 6 | 7 | 8 |
| 1 | 2 | 3 | 4 | 5 | 6 | 7 | 8 |
| 1 | 2 | 3 | 4 | 5 | 6 | 7 | 8 |

FIG. 5

| 9 | 10 | 11 | 12 | 13 | 14 | 15 | 16 |
|---|----|----|----|----|----|----|----|
| 9 | 10 | 11 | 12 | 13 | 14 | 15 | 16 |
| 9 | 10 | 11 | 12 | 13 | 14 | 15 | 16 |
| 9 | 10 | 11 | 12 | 13 | 14 | 15 | 16 |
| 9 | 10 | 11 | 12 | 13 | 14 | 15 | 16 |
| 9 | 10 | 11 | 12 | 13 | 14 | 15 | 16 |
| 9 | 10 | 11 | 12 | 13 | 14 | 15 | 16 |
| 9 | 10 | 11 | 12 | 13 | 14 | 15 | 16 |
| 9 | 10 | 11 | 12 | 13 | 14 | 15 | 16 |
| 9 | 10 | 11 | 12 | 13 | 14 | 15 | 16 |
| 9 | 10 | 11 | 12 | 13 | 14 | 15 | 16 |
| 9 | 10 | 11 | 12 | 13 | 14 | 15 | 16 |
| 9 | 10 | 11 | 12 | 13 | 14 | 15 | 16 |
| 9 | 10 | 11 | 12 | 13 | 14 | 15 | 16 |
| 9 | 10 | 11 | 12 | 13 | 14 | 15 | 16 |
| 9 | 10 | 11 | 12 | 13 | 14 | 15 | 16 |

FIG. 6

| N-7 | N-6 | N-5 | N-4 | N-3 | N-2 | N-1 | N |
|-----|-----|-----|-----|-----|-----|-----|---|
| N-7 | N-6 | N-5 | N-4 | N-3 | N-2 | N-1 | N |
| N-7 | N-6 | N-5 | N-4 | N-3 | N-2 | N-1 | N |
| N-7 | N-6 | N-5 | N-4 | N-3 | N-2 | N-1 | N |
| N-7 | N-6 | N-5 | N-4 | N-3 | N-2 | N-1 | N |
| N-7 | N-6 | N-5 | N-4 | N-3 | N-2 | N-1 | N |
| N-7 | N-6 | N-5 | N-4 | N-3 | N-2 | N-1 | N |
| N-7 | N-6 | N-5 | N-4 | N-3 | N-2 | N-1 | N |
| N-7 | N-6 | N-5 | N-4 | N-3 | N-2 | N-1 | N |
| N-7 | N-6 | N-5 | N-4 | N-3 | N-2 | N-1 | N |
| N-7 | N-6 | N-5 | N-4 | N-3 | N-2 | N-1 | N |
| N-7 | N-6 | N-5 | N-4 | N-3 | N-2 | N-1 | N |
| N-7 | N-6 | N-5 | N-4 | N-3 | N-2 | N-1 | N |
| N-7 | N-6 | N-5 | N-4 | N-3 | N-2 | N-1 | N |
| N-7 | N-6 | N-5 | N-4 | N-3 | N-2 | N-1 | N |
| N-7 | N-6 | N-5 | N-4 | N-3 | N-2 | N-1 | N |

FIG. 7

| 1 | 2 | 3 | 4 | 5 | 6 | 7 | 8 |
|---|---|---|---|---|---|---|---|
| 9 | 10 | 11 | 12 | 13 | 14 | 15 | 16 |
| 17 | 18 | 19 | 20 | 21 | 22 | 23 | 24 |
| 25 | 26 | 27 | 28 | 29 | 30 | 31 | 32 |
|  |  |  |  |  |  |  |  |
|  |  |  |  |  |  |  |  |
|  |  |  |  |  |  |  |  |
|  |  |  |  |  |  |  |  |
|  |  |  |  |  |  |  |  |
|  |  |  |  |  |  |  |  |
|  |  |  |  |  |  |  |  |
| N-23 | N-22 | N-21 | N-20 | N-19 | N-18 | N-17 | N-16 |
| N-15 | N-14 | N-13 | N-12 | N-11 | N-10 | N-9 | N-8 |
| N-7 | N-6 | N-5 | N-4 | N-3 | N-2 | N-1 | N |

METHOD FOR PREPARING ASSAY SUPPORTS HAVING AN ORDERED SET OF REACTION ZONES

BACKGROUND OF THE INVENTION

The present invention concerns the area of assaying chemical or biological substances, such as sequences of nucleic acids or proteins by specific reaction with a set of specific reagents fixed on a support. It relates more particularly to the assay of nucleic acids by hybridisation with oligonucleotide probes fixed on a support. This type of assay finds application in sequencing, diagnosis or quality control for research or industrial production.

The match law A-T (or A-U) and G-C gives nucleic acids the property of forming specific hybridisation complexes between complementary sequences. This long known hybridisation property means that a fragment of nucleic acid, or an oligonucleotide, can be used to display the presence of a complementary nucleic sequence. The analysis of DNA fragments after gel separation (E. Southern, J. mol. Biol., 1975, 98, 503–517) is today largely used both in the area of fundamental research and in medical analysis (Caskey, Science, 1987, 236, 1223–1228; Landegrer et al., Science, 1988, 242, 229–237; Arnheim et al., Ann rev. Biochem., 1992, 61, 131–156).

Several assay techniques of nucleic acids based on their hybridisation property with probes have been developed, in particular for the sequencing of unknown DNAs or RNAs, the detection of sequences associated with a pathology, and the search for point mutations in sequences (S. Ikata et al., Nuclei Acids Res., 1987, 15, 797–811; J. A. Matthews, L. J. Krieka, Analytical Biochemistry, 1988, 169, 1–25).

More recently, new assay methods for unknown DNA fragments have been put forward, based on hybridisation with a series of oligonucleotides comprising 5 to 9 bases arranged in known sequence and immobilised on a solid support (E. Southern, European Patent published under number: 0 373 203; K. R. Khrapko et al., FEBS Letters, 1989, 256, 118–122 ; R. Drmanac et al., Genomics, 1989, 4, 114–128 ; R. Drmanac et al., DNA and Cell Biology, 1990, 9, 527–534 ; K. R. Khrapko et al., J. DNA Sequencing Mapp., 1991, 1, 375–388 ; R. Drmanac et al., Science 1993, 260, 1649–1652 ; R. J. Lipshutz, J. Biomol. Struct. Dyn., 1993, 11, 637–653; U. Maskos, E. Southern, Nucleic Acids Res., 1993, 21, 4663–4669 ; A. C. Pease et al., Proc. Natl. Acad. Sci., USA, 1994, 91, 5022–5026; J. C. Williams, Nucleic Acids Res., 1994, 22, 1365–1367 ; E. M. Southern, Nucleic Acids Res., 1994, 22, 1368–1373.

These new assay methods are based on the preparation of a support on whose surface is fixed a series of oligonucleotide sequences having the same length covering all possible sequences for this length, each of the oligonucleotide sequences occupying cells, or zones, separated on the support. The preparation and use of said support is described in particular in European patent applications published under N°s 373 203 and 392 546 and in international patent application published under n° WO 94/12670. The sequence of nucleic acid to be assayed is labelled and applied to the support under conditions allowing hybridisation with the oligonucleotides, then after washing, the localisation of the labelling is noted on the support surface in order to detect the signals transmitted by any hybrids which may be formed between the assayed, labelled DNA fragment and one or more oligonucleotides of the series immobilised on the solid support. Each position shown to be positive on the support corresponds to a complementary sequence thus identified in the assayed DNA fragment.

Immobilisation of the oligonucloetides on the support surface may be conducted in accordance with two principles: either immobilisation after synthesis of the oligonucleotides, or direct synthesis of the oligonucleotides on the support.

Immobilisation after synthesis of the oligonucleotides is difficult to implement and does not appear sufficiently reproducible as is the case for antibodies ( European patent N° 0 063 810), therefore most teams working on this subject have chosen to develop techniques for direct synthesis on the support to be used for hybridisation and detection (International Patent Applications WO 90 03 382, WO 90 15 070, WO 91 08 307, WO 91 07 087, WO 92 10 092, WO 92 10 587, WO 93 10 161, WO 93 09 668, WO 94 22 889, WO 95 11 748, WO 95 30 774). These involve the synthesis one same surface of a series of oligonucleotide sequences having the same length covering all possible sequences for this length. Therefore, for oligonucleotides with 2 bases, chosen from among the four forming the DNA, 16 sequences are possible, for oligonucleotides with 3 bases 64 sequences are possible, for oligonucleotides with 4 bases 256 sequences are possible, for oligonucleotides with 5 bases 1024 sequences are possible, for oligonucleotides with 6 bases 4096 sequences are possible etc.. The shorter the oligonucleotide sequence, the less information it provides for sequencing; for a DNA fragment with arrangement, all or part of said homogeneous supports are mutually combined to form assay supports each having an ordered set of reaction zones of N different types or less.

DETAILED DESCRIPTION OF THE INVENTION

By "type of reaction " is meant the specific reaction likely to occur between the assayed substance and the support, when they are brought into contact. This reaction is determined by the nature of the different N reagents, present in ordered and verifiable manner on the supports obtained by the method of the invention, each of the initial N supports being homogeneous for one of its reagents. For the assay of nucleic acids, by type of reaction is meant the specific hybridisation reaction likely to occur between an oligonucleotide sequence fixed on one of the initial N supports, re-detected in a reaction zone on the final support, and a complementary nucleic acid sequence present in the assayed substance.

According to one first particular embodiment, the method of the invention comprises the following stages:

a) preparation of N flat shaped supports homogeneous for a type of reaction;

b) cutting said flat, homogeneous N supports into strips of substantially equal width;

c) combining substantially side by side the strips derived from at least one part of the N homogeneous supports so as to prepare intermediate supports which, along an axis that is perpendicular to said strips of homogeneous supports, comprise alignments of different reaction zones, each of said alignments of one same intermediate support being identical;

d) cutting the intermediate supports into strips of substantially the same width, each of said strips comprising one of said alignments of different reaction zones, e) combining substantially side by side the strips which each comprise an alignment of different reaction zones, in such manner as to form assay supports each having alignments of ordered reaction zones of N different types or less.

According to a second particular embodiment, the method of the invention comprises the following stages:

a') preparation of N homogeneous supports in the form of filaments or fibres, and b') combining substantially side by side several of said filaments in such manner as to prepare intermediate supports which, along an axis perpendicular to said filaments, comprise alignments of different reaction zones, each of said alignments of one same intermediate support being identical, then, carrying out stages (d) and (e) previously described in the first embodiment.

Stage (b') above may consist of gluing side by side the homogeneous filaments prepared in stage (a') so as to form the intermediate supports defined in stage (c) of the first embodiment.

One variant of stages (a) and (a') described above, consists of:

a") preparing N homogeneous supports in the form of filaments, and proceeding with weaving each of said N filaments with a weft made of reactively neutral strand so as to prepare the N homogeneous supports of the type of those in stage (a) described in the first embodiment, then, carrying out stages (b), (c), (d) and (e) previously described.

One variant of stages (a") and (b') described above consists of:

a') preparing N homogeneous supports in the form of filaments, and b") proceeding with weaving all or part of the homogeneous N filaments by intertwining a weft made of said N filaments with a strand that is reactively neutral, so as to prepare intermediate supports or a final support, then optionally carrying out stages (d) and (e) described previously, if the supports prepared at stage (b") are intermediate supports.

In order to maintain the rigidity of the intermediate support of stages (b), (b')and (b"), it is advantageously fixed to an auxiliary element for temporary or permanent support; "temporary" meaning that the auxiliary support element is removed after stage (e) or (b"), "permanent" meaning that the auxiliary support element is left in place after stage (e) or (b").

Also, the final support obtained at stages (e) and (b") may advantageously be made rigid and therefore handled with greater ease if it is fixed onto a support element. Also, this support element may be used to give a particular shape to the final support, such as for example one or more recesses to facilitate and border the deposits of hybridisation and revealing reagents at each reaction zone, or even to form an edge for the support.

The homogeneous supports of flat shape or in fibre form may be in a porous or non-porous matter. As porous flat support, preference is given to a cellulose microporous membrane.

If the support of the invention is intended to be used for the assay of nucleic acids, the initial N supports are each homogeneous for one type of specific hybridisation reaction. Advantageously, each of the N homogeneous supports then comprises a different oligonucleotide sequence. In one particular embodiment, intended for the sequencing or assay of mutations, on each of the N homogeneous supports is fixed a different oligonucleotide sequence but of similar length, all the oligonucleotide sequences of the N supports then covering all the possible sequences for this length.

Assay of the extent of hybridisation with each of the oligonucleotides, for example using the Tm values, at each reaction zone of the supports, can determine with great precision the sequence of the assayed nucleic acid, DNA or RNA or the presence of a mutation.

The supports of the inventions may also be used for immunological assay; in this case, the N supports are each homogeneous for one type of antigen-antibody reaction. In this embodiment, one different antibody or one antigen, according to whether the assayed substance is an antigen or an antibody, is fixed by any method known to men of the art on each of the initial N supports.

The supports of the invention may also be used for the assay of substrates likely to react with a series of different enzymes each placed at the level of each reaction zone.

The invention also relates to an assay support prepared using the above-described methods, and the use of this support for methods of assaying chemical or biological substances, and its incorporation into assay kits for chemical or biological substances.

Other characteristics and advantages of the invention will become apparent on reading the following examples which are given for guidance purposes and are not restrictive.

BRIEF DESCRIPTION OF THE DRAWINGS

One example of the method for preparing an assay support of the invention comprises stages (a) to (e) described below with reference to FIGS. 1 to 7 of the appended drawings.

a) N homogeneous supports are prepared for one type of reaction, for example, by fixing a different oligonucleotide sequence on each of the N supports.

For a clearer understanding of the method of the invention, FIGS. 1, 2 and 3 only show three supports of a series of N homogeneous supports of flat shape:

the support in FIG. 1 is homogeneous for the type of reaction referenced (1) corresponding to a first nucleic sequence;

the support in FIG. 2 is homogeneous for the type of reaction referenced (2) corresponding to a second nucleic sequence;

the support in FIG. 3 is homogeneous for the type of reaction referenced (N) corresponding to a nth nucleic sequence.

b) In each of the N homogeneous supports, strips of substantially the same width are cut as shown by the vertical lines in FIGS. 1, 2 and 3; therefore each of the homogeneous supports of FIGS. 1 to 3 is cut into 9 strips.

c) Using these strips, the intermediate supports of FIGS. 4, 5 and 6 were prepared by placing strips derived from stage (b) side by side, on an auxiliary support element, It can be easily seen that, along the horizontal axes perpendicular to the strips derived from the homogeneous supports, each of the intermediate supports comprises alignments of different reaction zones, each of said alignments of one same intermediate support being identical. FIGS. 4, 5 and 6 show three of these intermediate supports, each made up of 8 strips prepared at stage (b)

The support in FIG. 4 comprises 8 different vertical strips each carrying the same type of reaction zone, and 15 identical horizontal strips each comprising an alignment of 8 reaction zones of different types referenced: 1, 2, 3, 4, 5, 6, 7 and 8.

The support in FIG. 5 comprises an identical layout to that in FIG. 4, but with an alignment of 8 reaction zones of different type to those of the support in FIG. 4 referenced: 9, 10, 11, 12, 13, 14, 15 and 16.

the support in FIG. 6 represents the last intermediate support of the series of intermediate supports, on which the strips are laid out as in FIGS. 4 and 5 with an alignment of 8 different reaction zones referenced: N-7, N-6, N-5, N-4, N-3, N-2, N-1 and N.

d) the intermediate supports prepared at stage (c) were cut into strips of substantially the same width, each of said strips comprising one of said alignments of different reaction zones. In this way, from each intermediate support, a set of identical strips is obtained, each set being different. The set of strips derived from the intermediate support in FIG. 4 comprises 15 strips of different zones referenced: 1, 2, 3, 4, 5, 6, 7 and 8; the set of strips derived from the intermediate support in FIG. 5 comprises 15 strips of different zones referenced: 9, 10, 11, 12, 13, 14, 15 and 16, the set of strips derived from the intermediate support in FIG. 6 comprises 15 strips of different zones referenced: N-7, N-6, N-5, N-4, N-3, N-2, N-1 and N.

e) the assay supports are prepared by placing side by side, on a permanent support element, a strip of each of the sets of identical strips prepared at stage (d) in such manner that each of the assay supports contains the N different reaction zones. The example of FIG. 7, shows one of the 15 assay supports which may be obtained by using all the strips of stage (d).

I—Preparation of the N Homogeneous Supports of Stage (a)

1) Support Structure

The homogeneous supports of stage (a) may be porous or non-porous, and of flat or fibrous shape. By way of example, the supports of table I below can be cited.

TABLE I

| SUPPORTS | Flat | Fibrous |
|---|---|---|
| Non-porous | sheets, films | strands, meshes mono-filaments, |
| Porous | paper, non-woven sheeting, micro and ultra-filtration membranes | strands, multi-filaments, hollow fibres for micro and ultrafiltration. |

The choice of a porous or non-porous support is dependent upon the density of the reagents it is desired to deposit at each reaction zone. Owing to the greater available surface area, porous supports offer the possibility of achieving high molecule density.

The preferred porous supports of flat shape are microfiltration membranes with a pore size of between 0.1 and 10 $\mu$m and a thickness of between 50 and 150 $\mu$m. Strands are also a porous support of interest as they combine large surface area with high mechanical stability and their thickness is between 50 and 500 $\mu$m.

2) The Matter of Which the Support is Made

The matter of which the homogenous support is made having either a porous or non-porous structure, of fibrous or flat shape as described above, is generally an organic polymer, but in some cases, such as sheets or films, it may be a metal, aluminum for example. If the reagent elements are fixed chemically by covalent bonds with the support, any polymer allowing this type of bonding may be used. Among the latter, mention may be made of cellulose, polyamides, polyurethanes, polystyrenes and polyacrylonitryls or their derivatives. In the case of microfiltration membranes or fibres, preference is given to cellulose however as this material combines good chemical reactivity with strong stability against heat and organic solvents, high hydrophylicity and low non-specific absorption. The hydrophylic property is of importance for wetting with aqueous samples. The cellulose used may be in natural or fibrous form, for example of cotton filament type, but may also be of regenerated product type, such as viscose fibres. Microporous cellulose membranes, in all cases, contain regenerated cellulose, obtained by saponification of cellulose acetate membranes.

Conversely, strong absorption of the support is prejudicial if the reagent elements are fixed on the support by absorption. Antigens and antibodies are easily absorbed on cellulose nitrate. Polyamides are also of interest if absorption is used to fix the reagent elements on the support, also hydrophobic polymers such as polyolefins (polyethylene and polypropylene), polysulphones and polyethersulphones.

3—Type of Reaction

The reagents which may react with the assayed substance at each reaction zone are fixed on the supports using known chemical or physical methods of the prior art. They may be antigen proteins able to react with an antibody, or conversely antibodies able to react with a protein or part of a protein. They may also, and it is one of the main applications of the invention, be probe oligonucleotides, which are fixed on the previously described support using any method known to men of the art. Immobilisation may be made after synthesis of the oligonucleotide, or direct synthesis of the oligonucleotides on the support may be made using covalent bonds or a fixation arm which may assume the prior preparation of the N supports. Physical fixation may also be conducted, by absorption, ion exchange, chelate formation or any other equivalent technique known to men of the art.

II—Preparation of the Strips and Intermediate Supports of Stages (b) and

1) The Strips

If the support prepared at stage (a) is flat, it is cut directly into strips. For fibrous supports, these are advantageously fixed on a support element. If N is a number of great size, it is preferable that strip width should be as narrow as possible in order to achieve assay supports of small size. Therefore, a strip width of approximately 0.1 mm seems reasonable taking into account the cutting means available. For other applications, in which the size of the assay support is not critical, it is possible to use strips with an approximate width of 5 mm.

2) Intermediate Supports

The strips or fibres are placed on the auxiliary support elements, either side by side, or directly in contact with one another, or leaving a small space in the region of 0.1 to 1 mm between two strips in order to facilitate accurate positioning of each strip.

The auxiliary support element is a sheet or flat film in any type of material able to stabilize the strips forming the intermediate support and the final support.

The use of these auxiliary support elements may be solely temporary, the final assay support being removed from the auxiliary support element at the end of the process, or it may be permanent, the auxiliary support element then forming an integral part of the assay support of the invention. It is generally preferred to make temporary use of these auxiliary support elements.

In the event of permanent use, the fixation of the strips on the auxiliary support elements must be stable in order not to interfere with assay conditions when the support is used, for example, with hybridisation conditions if the reagent elements of the reaction sites are oligonucleotides.

Permanent fixation of the strips on the auxiliary support element may be made by various means; it may be achieved by heat lamination for example, welding, gluing. For strips prepared from homogeneous supports made of microporous cellulose membranes, they may be fixed in permanent manner on a polyolefin sheet (polypropylene, polyethylene or a mixture thereof) by heat lamination. In this case, the sheet is heated under pressure to the region of its melting point so that the melted product penetrates the membrane pores and creates a homogeneous mechanical bond between the support and the auxiliary support element after cooling. Another possibility consists of using reactive adhesives and resins, especially containing epoxides, urethanes or acrylates. Generally, non-reactive adhesives do not offer sufficient adhesive stability in the wet state.

Temporary fixation of the strips on the auxiliary support element may be made by heat lamination at temperatures and/or pressures that are insufficient to produce permanent fixation, or using adhesives having low adhesivity. As an example, an adhesive cartridge can be used of the type marketed by Beiersdorf (Hamburg, Germany) under the name "Tesafilm".

III—Cutting the Intermediate Supports of Stage (d)

The intermediate supports prepared in the previous stage are made up of strips derived from several initial homogeneous supports fixed on the auxiliary support element. These supports must be cut with great precision and the cutting stage is therefore a critical phase. The initial homogeneous support strips and the auxiliary support element must not be damaged ; also the position of the homogeneous support strips on the auxiliary element must not be changed when cutting. The lower limit of the width of the strips cut in the intermediate support depends upon the means available for cutting and holding the support. The standard most sophisticated means such as Laser can achieve a width of approximately 0.1 mm, but generally a strip width greater than that of the strips prepared in stage (b) is tolerated. If, for example, a strand having a thickness of 50 $\mu$m is used to prepare the homogeneous support, a cutting width at stage (d) in the region of 1 to 2 mm can allow a great number of reagent molecules to be fixed at a reaction zone. However, for certain applications in which the number of reagent molecules is not critical, the width of the strips prepared at stages (b) and (d) may be in the region of several millimeters.

IV—Preparation of the Assay Supports of Stage (e)

The assay supports must be geometrically stable at every stage of application. They must not bulge or shorten, for example when they are submitted to hybridisation conditions, they must remain sufficiently rigid so that they can be easily handled. Polymer films or sheets have these properties; among the latter mention may be made of the following examples: a film of polyethyleneglycolterephtalate, having a thickness of 50 to 500 $\mu$m, advantageously from 100 to 250 $\mu$m, or polyolefin sheets having similar thickness.

If at stage (c) the homogeneous support strips of stage (a) were fixed on auxiliary support elements in permanent manner, the assay supports are prepared by fixing the strips prepared at stage (d) side by side on a permanent support element; the side of the strips which is fixed on the permanent auxiliary support element is the side corresponding to the auxiliary support element.

If at stage (c) the intermediate support strips were fixed in temporary manner on the auxiliary support element, the assay supports are prepared by fixing the strips prepared at stage (d) side by side on a permanent support element ; the side of the strips which is fixed on the permanent support element is the side corresponding to the homogeneous support strips, the auxiliary support element being removed. Final fixation of the strips on the permanent support element is conducted as described in stage (c) for permanent fixation of the strips on the auxiliary support elements.

V—DETAILED EXAMPLES

1) Example n° 1 a) N microporous membranes of regenerated type SM 18606 marketed by Sartorius AG (Göttingen, Germany) are used having a pore size of 0.45 $\mu$m. On each of these N membranes, direct synthesis is made or a type of oligonucleotide sequence is fixed so as to obtain N membranes each being homogeneous for one type of the N oligonucleotide sequences pre-determined in relation to the sequences of nucleic acids it is desired to assay.

b) Synthesis of the N oligonucleotides of pre-determined sequences may be made with an automatic synthesizer using the phosphoramidite method, either directly on the membranes determined above under (a), or on another synthesis support, and in this case by detaching the oligonucleotides from the synthesis support during the last deprotection stage, then by fixing the oligonucleotides by any appropriate function on the cellulose membranes determined under (a).

c) Strips having a width of 2 mm are cut in each of the N homogeneous supports previously prepared, then the different strips are placed side by side on sheets of a polypropylene and polyethylene mixture of FO 2432 type, FA Freudenberg, and submitted to lamination at a temperature of 130–135° C. under a pressure of 10N/cm$^2$ and a speed of 5 m/min (length heated: 1.5 m).

The intermediate supports prepared in this way are cut in turn into strips 2 mm wide perpendicular to the cutting direction of the initial homogeneous N supports, then deposited with their sheet on a second sheet, laminated a second time under the same conditions as previously.

2) Example n° 2

Identical to example 1, but at the last stage the strips are glued with an acrylate adhesive of Macbond B2112 type, Fa. Mantac on one side onto a polymer film, and on the other side onto a polyester film of BN 180 type, Fa. Kalle, Wiesbaden.

3) Example n° 3

N homogeneous cotton filaments 200 $\mu$m thick each carrying a different oligonucleotide sequence are prepared as in example 1 for a cellulose membrane.

Different filaments are glued side by side on adhesive cartridges of "Scotch Klebeband ablösbar" type made by 3 M (USA) which are cut into strips 5 mm wide in a direction perpendicular to the filament. The strips prepared in this way are glued onto a Macbond B 212 cartridge on the filament side, whereas the other side of the Macbond cartridge is glued to a polyester film as in example 2, and the Scotch cartridge strips are removed to provide access to the filament pieces.

What is claimed is:

1. A method for preparing supports for assaying a chemical or biological substance, said supports each having an ordered set of reaction zones, the method comprising:
   (a) preparing a set of homogeneous strips for each reaction zone,
   (b) grouping several of said strips from step (a) substantially edge to edge so as to prepare intermediate supports which, along an axis perpendicular to said strips, comprise alignments of different reaction zones, and which, along a second axis comprise alignments of identical reaction zones,
   (c) cutting each intermediate support into a second set of strips, having substantially the same width, each of said strips from the second set of strips comprising one of said alignments of different reaction zones, and
   (d) grouping the strips from step (c) each comprising an alignment of different reaction zones substantially edge to edge so as to form assay supports each having alignments of ordered reaction zones of different types.

2. A method according to claim 1, wherein the intermediate support is fixed onto a temporary or permanent auxiliary support element.

3. A method according to claim 1, wherein the assay support is fixed on a support element.

4. A method for preparing supports for immunological assays according to claim 1, wherein the homogeneous strips are homogeneous for one type of antigen-antibody reaction.

5. A support for the assay of chemical or biological substances prepared by a method according to claim 1.

6. A method for the assay of chemical or biological substances, wherein the method is conducted with at least one support defined in claim 1.

7. An assay kit for chemical or biological substances, wherein the kit comprises at least one assay support defined in claim 1.

8. A method according to claim 1, wherein the homogeneous strips are in a porous or non-porous matter.

9. A method according to claim 8, wherein the homogeneous strips are cellulose membranes.

10. A method for preparing supports for the assay of nucleic acids in accordance with claim 1, wherein the homogeneous strips are homogeneous for a type of specific hybridization reaction.

11. A method according to claim 1, wherein a different oligonucleotide sequence is fixed on each set of homogeneous strips.

12. A method according to claim 11, wherein a different oligonucleotide sequence of equal length is fixed on each set of homogeneous strips, all the oligonucleotide sequences of each set of homogeneous strips covering all the possible sequences for this length.

13. A method according to claim 1, wherein the homogeneous strips are prepared from a homogeneous support of flat shape.

14. A method according to claim 13, wherein the homogeneous strips are prepared by cutting the homogeneous support into strips of substantially the same width.

15. A method according to claim 1, wherein the homogeneous strips are in filament form.

16. A method according to claim 15, wherein the homogeneous strips in filament form are woven with a strand made of reactively neutral thread to prepare a homogeneous support of flat shape.

* * * * *

UNITED STATES PATENT AND TRADEMARK OFFICE
CERTIFICATE OF CORRECTION

PATENT NO. : 6,491,869 B1
DATED : December 10, 2002
INVENTOR(S) : Demmer et al.

It is certified that error appears in the above-identified patent and that said Letters Patent is hereby corrected as shown below:

Title page,
Item [74], *Attorney, Agent or Firm,* now reads "Hoffman & Baron, LLP; Irving M. Feit" and should read -- Hoffmann & Baron, LLP; Irving N. Feit --

Column 1,
Lines 56-57, now reads "N°s 373 203 and 392 546 and in international patent application published under n° WO 94/12670. The sequence...", and should read -- N°s 373 203 and 392 546. The sequence... --

Column 2,
Lines 7-9, now reads "sufficiently reproducible as is the case for antibodies (European patent N° 0 063 810), therefore...", and should read -- sufficiently reproducible, therefore... --
Lines 14-15, now reads "WO 94 22 889, WO 95 11 748, WO 95 30 774).", and should read -- WO 94 22 889, WO 95 11 748). --
Line 26, now reads "for a DNA fragment with arrangement,...", and should read --for a DNA fragment with 1000 bases to be sequenced, for example, any sequence of 3 bases will statistically occur at least fifteen times, and the probable occurrence of a sequence with 4 bases is statistically 4 times, whereas a sequence with 5 bases should statistically only occur once. Consequently, these techniques require the synthesis of several tens and even thousands of different oligonucleotides on one same surface, and repetition of this synthesis for all the prepared supports.
    It appears virtually impossible, in accordance with techniques of the prior art, to conduct dozens of different syntheses on one same support without generating errors, which are a source of non-conforming positions on each support. It is therefore not possible to guarantee the accuracy of the sequence of the different positions on each support assumed to be identical. Under these conditions, quality control procedure, to provide total guarantee of each position, becomes immensely difficult.

UNITED STATES PATENT AND TRADEMARK OFFICE
CERTIFICATE OF CORRECTION

PATENT NO. : 6,491,869 B1
DATED : December 10, 2002
INVENTOR(S) : Demmer et al.

It is certified that error appears in the above-identified patent and that said Letters Patent is hereby corrected as shown below:

Column 2 cont'd,
Line 26 cont'd,

The present invention sets out precisely to provide supports on whose surface, in set zones, reagents are fixed that are specific for a type of reaction with the assayed substance, more particularly oligonucleotide sequences, whose characteristics and positions are reproducible and verifiable in order to conduct quality control without difficulty.

This purpose is achieved with a method for preparing supports for the assay of chemical or biological substances, each having an ordered set of reaction zones in which said chemical or biological substances may possibly react. The method of the invention is characterised in that N different supports are prepared each being homogenous for a type of reaction, and in that, according to a pre-determined arrangement, ...--

Column 4,
Lines 20-22, now reads "are given for guidance purposes and are not restrictive.
BRIEF DESCRIPTION OF THE DRAWINGS
One example of the method for preparing an assay...", and should read --are given for guidance purposes and are not restrictive.
One example of the method for preparing an assay...--

UNITED STATES PATENT AND TRADEMARK OFFICE
CERTIFICATE OF CORRECTION

PATENT NO. : 6,491,869 B1
DATED : December 10, 2002
INVENTOR(S) : Demmer et al.

It is certified that error appears in the above-identified patent and that said Letters Patent is hereby corrected as shown below:

Column 6,
Lines 36-37, now reads "II-Preparation of the Strips and Intermediate Supports of Stages (b) and", and should read --II-Preparation of the Strips and Intermediate Supports of Stages (b) and (c)--

Signed and Sealed this

Twenty-second Day of July, 2003

JAMES E. ROGAN
*Director of the United States Patent and Trademark Office*